US009414753B2

(12) United States Patent
Chon et al.

(10) Patent No.: US 9,414,753 B2
(45) Date of Patent: Aug. 16, 2016

(54) APPARATUS AND METHOD FOR RESPIRATORY RATE DETECTION AND EARLY DETECTION OF BLOOD LOSS VOLUME (75) Inventors: Ki H. Chon, Worcester, MA (US); Nandakumar Selvaraj, Worcester, MA (US)

(73) Assignees: Worcester Polytechnic Institute, Worcester, MA (US); The Research Foundation of the State University of New York, Albany, NY (US)

( * ) Notice: Subject to any disclaimer, the term of this patent is extended or adjusted under 35 U.S.C. 154(b) by 13 days.

(21) Appl. No.: 13/503,075

(22) PCT Filed: Oct. 20, 2010

(86) PCT No.: PCT/US2010/053382
§ 371 (c)(1),
(2), (4) Date: Aug. 3, 2012

(87) PCT Pub. No.: WO2011/050066
PCT Pub. Date: Apr. 28, 2011

(65) Prior Publication Data
US 2012/0296219 A1 Nov. 22, 2012

Related U.S. Application Data (60) Provisional application No. 61/253,205, filed on Oct. 20, 2009, provisional application No. 61/392,287, filed on Oct. 12, 2010.

(51) Int. Cl.
A61B 5/02 (2006.01)
A61B 5/0205 (2006.01)
(Continued)

(52) U.S. Cl.
CPC ............ *A61B 5/02042* (2013.01); *A61B 5/021* (2013.01); *A61B 5/0816* (2013.01); *A61B 5/14551* (2013.01)

(58) Field of Classification Search
CPC .. A61B 5/02042; A61B 5/021; A61B 5/0816; A61B 5/14551
USPC ......... 600/479, 481, 483, 484, 500, 501, 502, 600/507, 529
See application file for complete search history.

(56) References Cited

U.S. PATENT DOCUMENTS 8,221,319 B2 * 7/2012 Lovejoy ........................ 600/364
8,251,912 B2 8/2012 Shelley et al.
(Continued)

FOREIGN PATENT DOCUMENTS

JP 2008036433 A 2/2008

OTHER PUBLICATIONS

International Search Report dated May 18, 2011 for PCT/US10/53382.

(Continued)

*Primary Examiner* — Long V Le
*Assistant Examiner* — Kevin Pontius
(74) *Attorney, Agent, or Firm* — Burns & Levinson LLP; Orlando Lopez (57) ABSTRACT An apparatus and method for non-invasive monitoring and detection of sudden changes in cardiovascular hemodynamics, in which a PPG signal is obtained from a patient, a time-frequency spectrum (TFS) is computed from the PPG signal, instantaneous modulations at a plurality of time points defining a curve of a prominent frequency of oscillation are extracted from the TFS, a peak power spectral density sequence is computed using the instantaneous modulations, and instantaneous peak values for following prominent frequency oscillations are monitored.

9 Claims, 11 Drawing Sheets (51) Int. Cl.
*A61B 5/024* (2006.01)
*A61B 6/00* (2006.01)
*A61B 5/021* (2006.01)
*A61B 5/08* (2006.01)
*A61B 5/1455* (2006.01)

(56) References Cited

U.S. PATENT DOCUMENTS

| | | | |
|---|---|---|---|
| 2004/0260186 A1 | 12/2004 | Dekker | |
| 2006/0058691 A1* | 3/2006 | Kiani | 600/507 |
| 2006/0074322 A1 | 4/2006 | Nitzan | |
| 2008/0067132 A1* | 3/2008 | Ross et al. | 210/739 |
| 2008/0188760 A1* | 8/2008 | Al-Ali et al. | 600/507 |
| 2013/0172760 A1* | 7/2013 | Chon et al. | 600/484 |
| 2013/0261415 A1* | 10/2013 | Ashe et al. | 600/324 |
| 2013/0276785 A1* | 10/2013 | Melker et al. | 128/204.23 |

OTHER PUBLICATIONS

International Preliminary Report on Patentability dated Apr. 24, 2012 for PCT/US10/53382.

Selvaraj, N. et al. A Novel Approach Using Time-Frequency Analysis of Pulse-Oximeter Data to Detect Progressive Hypovolemia in Spontaneously Breathing Healthy Subjects, IEEE Transactions on Biomedical Engineering, Aug. 2011, vol. 58, No. 8, pp. 2272-2279.

Chon, K. H. Estimation of Respiratory Rate From Photoplethysmogram Data Using Time-Frequency Spectral Estimation. IEEE Transactions on Biomedical Engineering, Aug. 2009, vol. 56, No. 8, pp. 2054-2063.

* cited by examiner

APPARATUS AND METHOD FOR RESPIRATORY RATE DETECTION AND EARLY DETECTION OF BLOOD LOSS VOLUME

CROSS REFERENCE TO RELATED APPLICATIONS

This application is the national phase entry under 35 USC §371 of International Patent Application No. PCT/US10/53382, titled APPARATUS AND METHOD FOR RESPIRATORY RATE DETECTION AND EARLY DETECTION OF BLOOD LOSS VOLUME, filed Oct. 20, 2010, which in turn claims priority of U.S. Provisional Application Ser. No. 61/253,205, filed on Oct. 20, 2009 and of U.S. Provisional Application Ser. No. 61/392,287, entitled SYSTEM AND METHOD FOR THE DETECTION OF BLOOD VOLUME LOSS, filed on Oct. 12, 2010, all of which are herein incorporated by reference in their entirety for all purposes.

GOVERNMENT SUPPORT

This invention was made with government support under grant number N00014-08-1-0244 awarded by the Office of Naval Research. The government has certain rights in the invention.

BACKGROUND OF THE INVENTION

1. Field of the Invention

The present invention relates generally to non-invasive hemodynamic monitoring and, more particularly, to a method and apparatus for detection of sudden blood loss by monitoring and processing of photoplethysmography (PPG) data.

2. Background of the Related Art

Real-time, accurate warning of impending hypovolemia remains elusive, and vital signs often do not substantially change between the times of hemorrhage until cardiovascular collapse. Conventional devices use a PPG signal to non-invasively detect blood and fluid loss. Conventional systems also observe respiratory-induced variations in PPG signal amplitude for exaggerations that might relate to blood volume loss in mechanically ventilated patients. However, the relevance, sensitivity and specificity of respiratory variation in PPG amplitude in awake, spontaneously breathing patients and healthy subjects has yet to be established.

Pulse oximetry is a commonly used noninvasive technique to continuously monitor arterial oxygen saturation ($SpO_2$) and Heart Rate (HR). A PPG sensor that comprises the pulse oximeter reflects changes in the light absorption of a vascular bed containing a pulsatile, arterial component, and a slowly varying venous component, related to the average blood volume and tissue properties.

Hemodynamic response to progressive acute hypovolemia is a complex process with two distinct phases. In a first phase, an arterial baroreceptor-mediated phase, a fall in cardiac preload is nearly matched by a sympathetically mediated increase in peripheral resistance so that arterial Blood Pressure (BP) is maintained near normal levels. When blood volume falls to a critical level, i.e. approximately thirty percent of a normal level, a second phase abruptly develops. The second phase is characterized by withdrawal of sympathetic vasoconstrictor drive, relative or absolute bradycardia, and a profound fall in arterial pressure. Blood flow to the brain and heart is compromises, posing a serious threat to life. Therefore, early detection of blood loss, such as from hemorrhage, remains a challenging task in emergency/critical care medicine, surgery and anesthesia, given the opacity of routinely measured vital signs such as HR and BP which reflect the symptoms of blood loss only after at least 30% of circulating blood volume is lost.

A major impediment in early detection of blood loss of conventional systems is quantifying respiratory variations directly from pulse oximetry. Towards this goal, the Power Spectral Densities (PSD) of the PPG signal has recently been used to calculate the ratio of the respiratory peak power to the heart rate peak power. The present invention identifies an increased ratio that occurs before statistically significant change in BP or HR. Using the PSD is better than time-domain approaches such as Plethysmogram Variability Index (PVI) or Partial Thromboplastin Time (PTT). However, use of PSD is not optimal since time-varying dynamics of the respiratory and heart rates, especially during blood loss, are not accounted for. Also, determining a precise location of the respiratory peak is problematic since the respiratory peak is often one of the smallest peaks in a spectrum, and becomes even more difficult to decipher once motion/noise artifacts appear.

To combat a part of these problems, a time-varying PSD approach has been developed utilizing a short-time Fourier transform (STFT). However, the STFT technique only partially solves the time-varying issue. Further, both the time and frequency resolutions are suboptimal, and not the most effective approach for early blood loss detection. To overcome these shortcoming, a method and apparatus for real-time continuous monitoring of blood volume loss capability is provided herein.

SUMMARY OF THE INVENTION

The present invention overcomes the shortcoming of conventional systems by providing a non-invasive monitoring apparatus that accurately detects, in real-time, blood or fluid loss to warn of impending hypovolemia, via processing of photoplethysmography data.

In a preferred embodiment, a method and apparatus are provided for non-invasive monitoring and detection of sudden changes in cardiovascular hemodynamics, in which a PPG signal is obtained from a patient, a time-frequency spectrum (TFS) is computed from the PPG signal, instantaneous modulations at a plurality of time points defining a curve of a first prominent frequency oscillation are extracted from the TFS, a peak power spectral density sequence is computed using the instantaneous modulations, and instantaneous peak values for following prominent frequency oscillations are monitored. In a preferred embodiment, for a mechanically ventilated patient an indication of hypovolemia is obtained by detecting increases in modulation of venous (DC) components of the PPG signal, typically with detection of the DC components being made in a range of 0.15-0.4 Hz, and for a spontaneously breathing patient an indication of hypovolemia is obtained by detecting increases in a predominantly arterial signal of the PPG signal, typically in a range of 0.8-1.5 Hz, thereby improving diagnosis and treatment of hypovolemia and hypovolumic conditions.

BRIEF DESCRIPTION OF THE FIGURES

The above and other objects, features and advantages of certain exemplary embodiments of the present invention will be more apparent from the following detailed description taken in conjunction with the accompanying drawings, in which.

DETAILED DESCRIPTION OF THE PREFERRED EMBODIMENTS

A description of detailed construction of preferred embodiments is provided to assist in a comprehensive understanding of exemplary embodiments of the invention. Accordingly, those of ordinary skill in the art will recognize that various changes and modifications of the embodiments described herein can be made without departing from the scope and spirit of the invention. Descriptions of well-known functions and constructions are omitted for clarity and conciseness.

The present invention utilizes a non-stationary spectral technique, Variable Frequency Complex Demodulation (VFCDM), which is time-varying and nonlinear, to detect consistent and statistically significant spectral amplitude or frequency changes during hypovolemia preferably by focused analysis of slowly varying venous components (DC) of a PPG signal in anesthetized, mechanically ventilated patients, see FIG. 4, and by focused analysis of Arterial Components (AC) of the PPG signal in spontaneously breathing patients, see FIG. 5, as described below. The AC components of the PPG signal in awake, spontaneously breathing subjects are predominantly arterial and can be extracted from the subject's heart rate frequency, e.g. 0.8-1.5 Hz, and the DC component, representing the respiratory frequency, between 0.15 and 0.4 Hz.

The present invention enables the PPG signal to be utilized for early diagnosis and quantification of hypovolemia at levels of blood loss not identified by changes in vital signs or physician estimation. Such use of PPG signal components to detect blood loss overcomes deficiencies in use of Blood Pressure (BP) and Heart Rate (HR), which do not show discernable changes up to thirty percent blood volume loss, particularly in healthy individuals.

In the preferred embodiments hardware and computational approaches are provided to combat motion artifacts. Motion artifacts are detected and removed from PPG recordings preferably using the techniques disclosed in U.S. patent application Ser. No. 11/803,771, published Nov. 20, 2008, as US-2008-0287815 A1, U.S. Provisional Patent Application No. 60/800,772, filed with the U.S. Patent and Trademark Office on May 16, 2006, U.S. Provisional Patent Application No. 61/392,287, filed with the U.S. Patent and Trademark Office on Oct. 12, 2010, and entitled SYSTEM AND METHOD FOR THE DETECTION OF BLOOD VOLUME LOSS, and U.S. Provisional Application No. 61/392,292, entitled SYSTEM FOR QUANTIFYING THE PRESENCE OF PHASE COUPLING USING THE BISPECTRUM, filed with the U.S. Patent and Trademark Office on Oct. 12, 2010, the contents of each of which are incorporated herein by reference.

In a first scenario, i.e. first mode, involving anesthetized, mechanically ventilated patients, an observed statistically significant change in the power spectral density of the AC component, as shown in FIG. 4, in the PPG reflects alterations in intravascular volume indicating hypovolemia. Conversely, in a second scenario, i.e. a second mode, involving spontaneously breathing patients, a statistically significant decrease in the AC components of the PPG reflects the alterations in intravascular volume indicating hypovolemia.

In the surgical procedure of the first scenario, patients undergoing elective lower abdominal procedures under general anesthesia in an operating room setting with blood loss anticipated greater than 500 cc were observed. Patients were intubated after induction of propofol (2.0-3.0 mg·kg-1 IV) and vecuronium (0.1 mg·kg-1 IV). Sevoflurane 1-3% in combination with nitrous oxide 60% in oxygen was administered for maintenance of anesthesia. The ventilator was set to a tidal volume of 10 cc/kg at I/E ratio of 1:2. At the end of surgery, inhaled anesthetics were discontinued and residual neuromuscular blockade reversed with neostigmine (0.05 mg·kg-1 IV) and glycopyrrolate (0.01 mg·kg-1 IV). During surgery, estimated blood loss as well as fluid replacement given to the patient was closely followed and recorded by observing clinicians.

In regard to the blood donation procedure for the second scenario, blood donation is known to elicit a decrease in central blood volume as a model of controlled, non-traumatic hemorrhage. Data recording was commenced at least fifteen minutes prior to cannulation and continued throughout the blood donation process in healthy, spontaneously breathing subjects in a semi-recumbent position. A 16-gauge intravenous catheter was inserted into an antecubital vein after local anesthetic to the skin and connected to standard blood collection bags, under supervision of a trained phlebotomist. Two units of blood (900 cc) were allowed to drain by gravity. Reinfusion of the same two units of blood was accomplished linearly over a period of 20 minutes, facilitated by the addition of 200 ml normal saline, allowing examination of VFCDMppg sensitivity in detecting blood volume loss at 450 cc.

A third scenario involving a Lower Body Negative Pressure (LBNP) experiment was also performed, simulating loss of approximately two liters of blood, with patients breathing spontaneously, with LBNP being recognized as an effective model of varying levels of hemorrhage including severe blood loss in conscious humans. Application of LBNP sequesters blood in the pelvis and leg regions, and induces magnitudes of central hypovolemia and autonomic compensation similar to those observed in acute hemorrhage. During the test, healthy subjects underwent a three minute baseline period followed by gradual exposure to −15, −30, −45, −60, −75 and −90 mmHg of decompression for at least two minutes at each level or until the onset of cardiovascular collapse or presyncopal symptoms.

Data acquisition was performed with a clinical dataset including multiple-site PPGs for the second and third scenarios, and only a finger PPG for the first scenario, with ECG signals, with continuous noninvasive arterial BP signals, with respiratory piezo-transducer signals, with $CO_2$, and with airwave pressure recordings. Echocardiography was also performed and three identical reflective infrared (approximately 940 nm) PPG probes (MLT1020; ADI Instruments, Colorado Springs, Colo.), in which auto-gain function and other filtering algorithms were disabled, placed via a clip at the finger, at the forehead covered by clear dressing, and clipped at ear for multiple-site recording. A nasal $CO_2$ waveform was obtained from an Ohmeda RGM gas monitor (model 5250, Datex-Ohmeda, Madison Wis.), and a respiratory belt transducer (MLT1132; ADI instruments) was placed around the chest for true respiratory recording will allow for independent detection of chest wall movement (via the respiratory belt) vs. ventilation (via the detection of CO2). In addition, standard surface ECG and routine noninvasive arterial BP were monitored. All noninvasive waveforms were recorded at 200 Hz with Powerlab/16SP with Quad Bridge Amp (ML795 & ML112; ADI instruments), providing a dataset of PPG recordings analyzed according to the preferred embodiments of the present invention. Parameters were obtained with TTE (via Q-Lab (Philips Medical, Andover, Mass.)), and correlated with simultaneous PPG measures: aortic flow, left ventricular end diastolic volume, left ventricular end systolic volume, maximum inferior vena cava diameter (IVCmax), minimum inferior vena cava diameter (IVCmin) and mitral inflow parameters. These parameters were used to calculate stroke volume, pre-ejection period and estimation of preload, to measure fluid responsiveness. These parameters, in particular the stroke volume derived from echocardiography, were compared to AC and DC values derived from VFCD-Mppg, as discussed herein.

Figure 8:
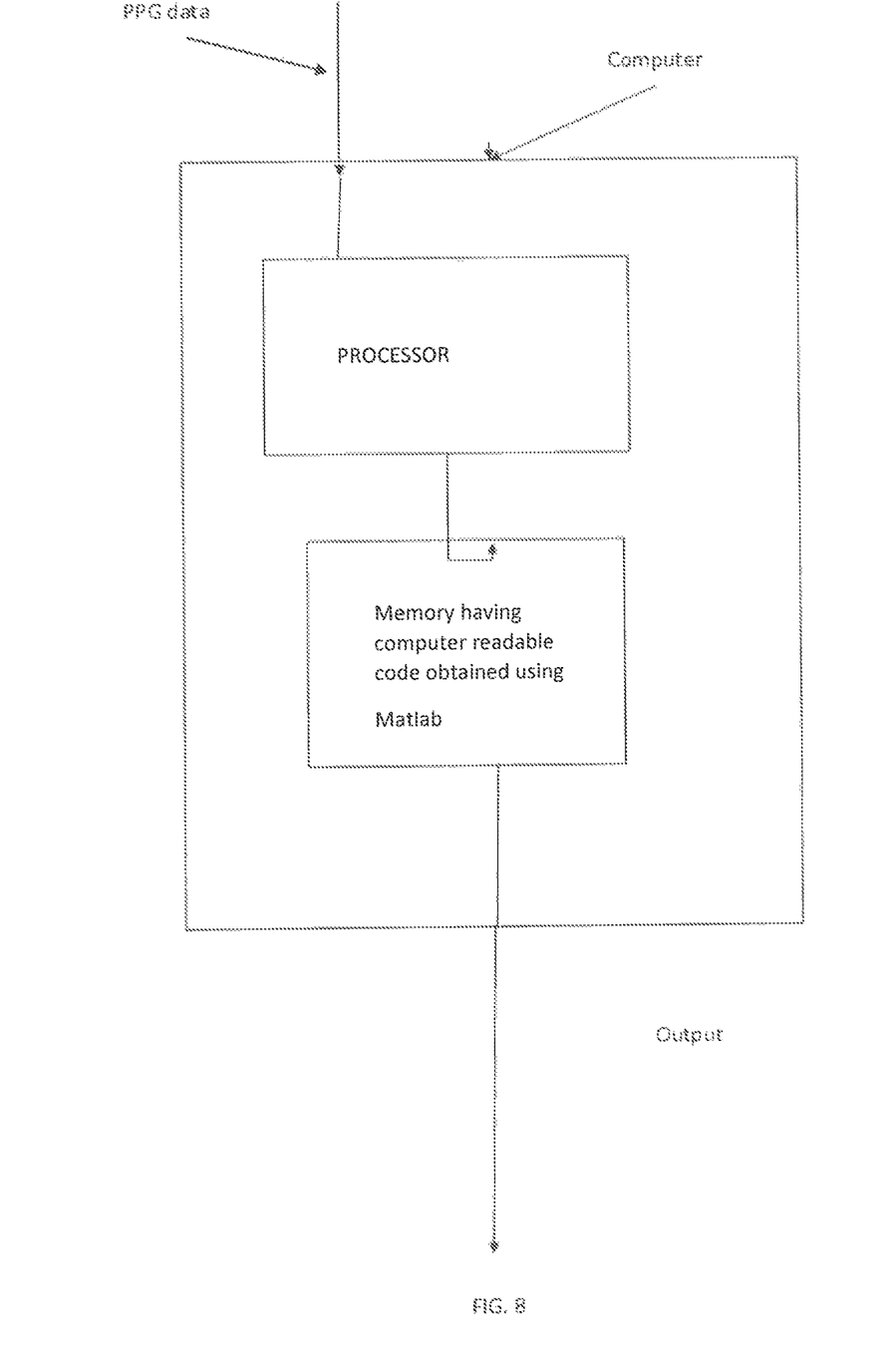
FIG. 8 is a schematic representation of a component using the analysis of data.

A VFCDM algorithm was utilized for continuous monitoring of intravascular blood volume. Instantaneous amplitude modulations present in cardiac (HR1.3±0.2 Hz, i.e. based on an individual subject's baseline HR) as well as respiratory band (0.05-0.35 Hz) frequencies of the PPG were extracted at every time instant as AC and DC components respectively using the Time-Frequency Spectrum (TFS) of VFCDM, as described herein and in U.S. patent application Ser. No. 11/803,771, to Chon, the contents of which are incorporated herein by reference. The recorded PPG data were analyzed offline using Matlab®. Before VFCDM analysis, the PPG signals were down sampled to 20 Hz, preprocessed, zero-meaned, linearly detrended and normalized to unit variance. FIG. 8 shows schematically the analysis of the data using Matlab®. As stated in U.S. patent application Ser. No. 11/803,771, in regard to complex demodulation methods for estimating TFS, a sinusoidal signal x(t) is considered to be a narrow band oscillation with a center frequency $f_0$, instantaneous amplitude A(t), phase $\phi(t)$, and the direct current component dc(t), as in Equation (1):

$$x(n)=dc(t)+A(t)\cos(2\pi f_0 t+\phi(t)) \quad (1)$$

For a given center frequency, instantaneous amplitude information A(t) and phase information $\phi(t)$ can be extracted by multiplying Equation (1) by $e^{-j2\pi f_0 t}$, resulting in Equation (2):

$$z(t) = x(t)e^{-j2\pi f_0 t} \quad (2)$$

$$= dc(t)e^{-j2\pi f_0 t} + \frac{A(t)}{2}e^{j\phi(t)} + \frac{A(t)}{2}e^{-j[4\pi f_0 t+\phi(t)]}$$

A leftward shift by $e^{-j2\pi f_0 t}$ results in moving the center frequency, $f_0$, to zero frequency in the spectrum of z(t). If z(t) in Equation (2) is subjected to an ideal Low-Pass Filter (LPF) with a cutoff frequency $f_c < f_0$, then the filtered signal $z_{lp}(t)$ will contain only the component of interest and the following Equations (3-5) are obtained:

$$z_{lp}(t) = \frac{A(t)}{2}e^{j\phi(t)} \quad (3)$$

$$A(t)=2|z_{lp}(t)| \quad (4)$$

$$\phi(t) = \arctan\left(\frac{\text{imag}(z_{lp}(t))}{\text{real}(z_{lp}(t))}\right) \quad (5)$$

When a modulating frequency is not fixed, as described above, but varies as a function $$x(t) = dc(t) + A(t)\cos\left(\int_0^t 2\pi f(\tau)d\tau + \phi(t)\right) \quad (6)$$

In regard to Equations (1)-(6) above, changing the center frequency followed by using the variable frequency approach of Equation (1) and Equation (6), respectively, as well as the LPF, the signal, x(t), will be decomposed into the sinusoid modulations by the CDM technique, as in Equation (9):

$$x(t) = \sum_i d_i = dc(t) + \sum_i A_i(t)\cos\left(\int_0^t 2\pi f_i(\tau)d\tau + \phi_i(t)\right) \quad (9)$$

The instantaneous frequency and amplitude of di is then calculated using a Hilbert transform. The entire time-frequency spectrum can be obtained by the calculation of the Hilbert transform of Equation (9) for all time points for the obtained low-pass filtered frequency components, as described in Equation (3). Therefore, by the combination of the CDM and Hilbert transform, a high TF resolution spectrum and accurate amplitude information is obtained. The procedure for implementing the CDM on a TFS is summarized immediately below and discussed in further detail herein.

1) Design a Finite Impulse Response (FIR) LPF with the bandwidth and the length of the filter set to $F_\omega$, and $N_\omega$, respectively. Set center frequencies, $f_{0i}=(i-1)(2F_\omega)$;

$$i = 1, \ldots, \text{int}\left(\frac{\text{max} freq}{2F_\omega}\right),$$

where the bandwidth between neighboring center frequencies is $2 \times F_\omega$, and max freq represents the highest signal frequency.

2) Use the fixed frequency of the CDM to extract the dominant frequency within the confined bandwidth and repeat it over the entire frequency band (by incrementing $f_{0i}$), referred to herein as Fixed-Frequency Complex Demodulation (FFCDM).
3) Decompose the signal into sinusoidal modulations via the CDM.
4) Calculate instantaneous frequencies (see Equation (19) below) based on the phase (Equation (18) below) and instantaneous amplitudes (Eq. (17) below) of each sinusoidal modulation component using the Hilbert transform.
5) Obtain TF representation of the signal using the estimated instantaneous frequencies and amplitudes.

6) For a variable frequency method, the first step is to use any of the time-frequency approaches (e.g., TVOPS, FFCDM, or smoothed pseudo Wigner-Ville (SPWV)) to obtain an estimate of the TFS. The center frequencies are the "backbones" of the time-frequency spectra, and only they are considered in subsequent analysis. This approach allows a considerable reduction in computation time since only a few frequencies (those of interest) are analyzed.

The FIR LPF has a filter bandwidth set to $F_y=F_\omega/2$, and a length of the filter is set to $N_y=N_w$ along estimated center frequencies $f_i(t)$. Further refined amplitude and phase information is extracted via steps 3-5, above, thereby further improving performance of any of the TFS including the FFCDM and TVOPS, and further improved time-frequency resolution is obtained.

Step 6 above is referred to herein as VFCDM, which is a two-step procedure, in which the first procedure involves using any of the time-frequency methods (e.g., TVOPS or FFCDM). The TVOPS is a recently developed algorithm THAT provides one of the most accurate TF spectra, mainly due to an accurate model order selection criterion. Zou, R., et al., *A Robust Time-Varying Identification Algorithm Using Basis Functions, Ann. Biomed. Eng.*, 31:840-53 (2003), generally describes the TVOPS. Choosing the FFCDM followed by the VFCDM is referred to as FF-VFCDM. Similarly, use of the TVOPS followed by the VFCDM is termed TVOPS-VFCDM.

By taking the Hilbert transform of x(t) in Equation (1), above, we obtain the following Equation (10):

$$s(t)=x(t)+j\text{Hilbert}[x(t)] \quad (10)$$

where s(t) is the analytic signal (real and imaginary) of x(t). $S_z(\omega)$ is denoted as the TFS of the signal obtained by the CDM.

Turning now to a combination of the TVOPS and VFCDM (TVOPS-VFCDM). The TVOPS algorithm is based on estimating only a few time-varying coefficients that best characterize the dynamics of the system to within a specified degree of accuracy, and is briefly described as follows.

In the Hilbert Transform, for an arbitrary time series, X(t), it is assumed that X(t) contains center frequency oscillations, i.e., $f_0$. The Hilbert transform, Y(t), is as provided in the following Equation (16):

$$Y(t) = H[X(t)] = \frac{1}{\pi}\int \frac{X(t')}{t-t'}dt' \quad (16)$$

An instantaneous amplitude is provided in Equation (17)

$$A(t)=[X^2(t)+Y^2(t)]^{1/2} \quad (17)$$

and an instantaneous phase is provided in Equation (18):

$$\varphi(t) = \arctan\left(\frac{Y(t)}{X(t)}\right) \quad (18)$$

The instantaneous frequency is provided in Equation (19):

$$f(t) = \frac{1}{2\pi}\frac{d\varphi(t)}{dt} \quad (19)$$

Statistical measures, such as the median and variance values of the AC and DC components, were computed for every second using a second moving window with a four second overlap. The five second moving window was chosen to smooth the spike variations in the AC and DC components with respect to every normal breath cycle, considering a twelve cycle/min normal respiration rate. The amplitude values of the AC and DC components, ratio of the DC/AC components of the VFCDM obtained for every second, and an area under the PSD curves of the AC and DC time series from 0.15-0.7 Hz were used to assess blood volume.

In operating room settings for the first scenario, blood loss quantification was approximated by assessment of drainage canisters and weighing of sponges. Further, a transesophageal echocardiogram (TEE) was used for involving expected large blood loss. In the blood withdrawal second scenario, the exact amount (cc's) of blood withdrawn was, whereas in the third LBNP scenario, the subject's blood volume loss was estimated from the TTE and the degree of chamber negative pressure, as known to correlate well with the amount of blood loss. Therefore, with the actual or deduced blood volume loss as a benchmark, VFCDM analysis were used to estimate blood volume loss noninvasively at various stages of each of the three scenarios. The sensitive PPG measures for the accurate detection of changes in blood volume loss was identified and appropriate threshold levels were evaluated to facilitate the early detection of blood volume loss associated with hypovolemia.

Preferred embodiments of the present invention utilize a method that distinguishes mechanically ventilated and spontaneously breathing patients, by differently analyzing the DC and AC components of the PPG signal to detect blood loss in either spontaneously or mechanically ventilated patients by use of the different reflected PPG signal dynamics for the dissimilar physiological conditions.

Preferred embodiments of the present invention determine the relative reliability and significance of the VFCDM of AC versus DC components of the PPG signal in blood loss detection in different patient populations, and utilize Multi-Channel Pulse Oximeter (MCPO) hardware to combat motion-artifact contamination to provide a robust, quantitative, sensitive and specific early detection system for blood loss based on obtained PPG signals, which is a noninvasive and inexpensive optical technology that monitors changes in blood flow in peripheral blood vessels.

In a preferred embodiment, the MCPO provides real-time continuous monitoring that simultaneously monitors blood loss, respiration rate, heart rate and arterial oxygen saturation ($SpO_2$), to improve and streamline patient care in surgery, acute trauma care, critical care, and anesthesia.

As show in FIGS. 1(a)-(f), a respiratory variation reflected in arterial pulse pressure or in the amplitude changes of the pulse oximeter is shown to be a good predictor of fluid responsiveness. FIGS. 1(a)-(f) show PPG waveforms and respective amplitude modulations from AC and DC components extracted from the Time-Frequency Spectrum (IFS) analysis. A baseline is shown in the left panel as FIG. 1(a) and a blood volume loss condition is shown in the right panel for a Lower Body Negative Pressure (LBNP) at −90 mmHg in FIG. 1(b), with an after spontaneous blood withdrawal of 900 cc shown in FIG. 1(d), and a blood loss of 1500 cc under mechanical ventilation shown in FIG. 1(f). The present invention identifies respiratory variations of pulse oximeter data that are subtle, nonlinear, time-varying and corrupted by motion artifacts, and provides early detection of blood volume loss, especially with spontaneously breathing subjects.

Respiratory amplitude variations from DC and AC components of the TFS are extracted, showing statistically significant changes during blood volume loss from mechanically (positive pressure) ventilated and spontaneously breathing subjects, respectively. Detection of blood volume loss in patients either with or without anesthesia requires quantification of amplitude variations from DC and AC components of the TFS, respectively.

Figure 1A:
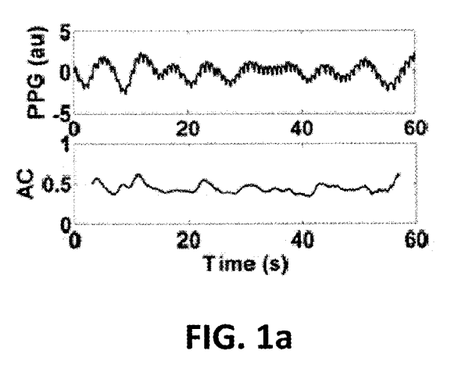
FIGS. 1(a)-(f) show PPG waveforms with respective AC and DC components extracted using TFS analysis of a frequency-domain technique, with Variable Frequency Complex Demodulation (VFCDM) signals in accordance with an embodiment of the present invention.
Figure 1B:
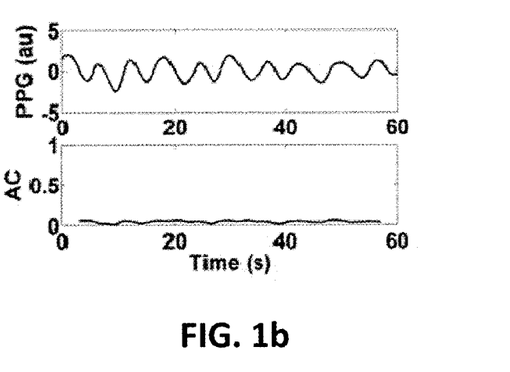
Figure 1C:
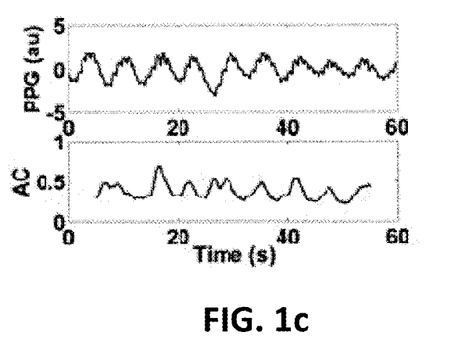
Figure 1D:
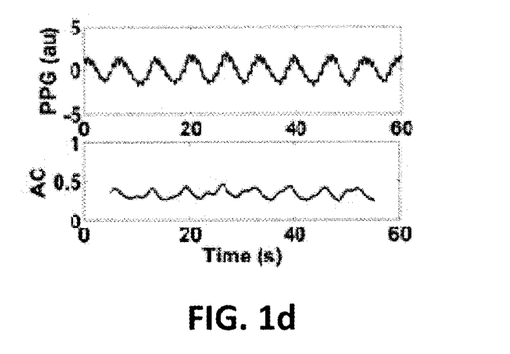
Figure 1E:
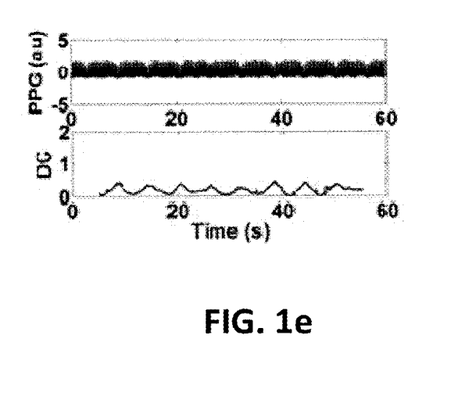
Figure 1F:
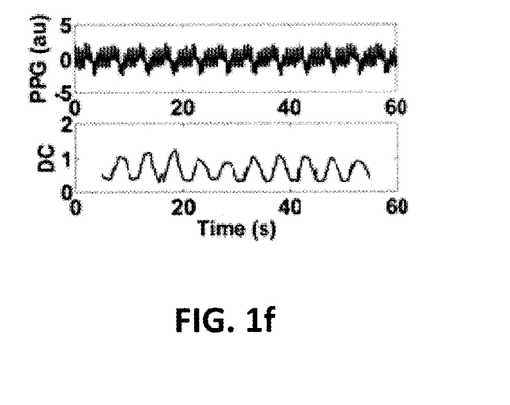

Referring to FIG. 1, the left panels, i.e. FIGS. 1(a), 1(c) and 1(e), show a baseline, and the right panels, i.e. FIGS. 1(b), 1(d) and 1(f), show blood volume loss. Data obtained from spontaneously breathing patients are shown in the middle 2 rows, i.e. FIGS. 1(c) and 1(d), and data obtained from mechanically ventilated patients is shown in the bottom 2 rows, i.e. FIGS. 1(e) and 1(f). As shown from the obtained data, the AC or DC components show changes indicative of a quantifiable blood volume loss, well in advance of either BP or HR changes showing such quantifiable blood volume loss.

Figure 2A:
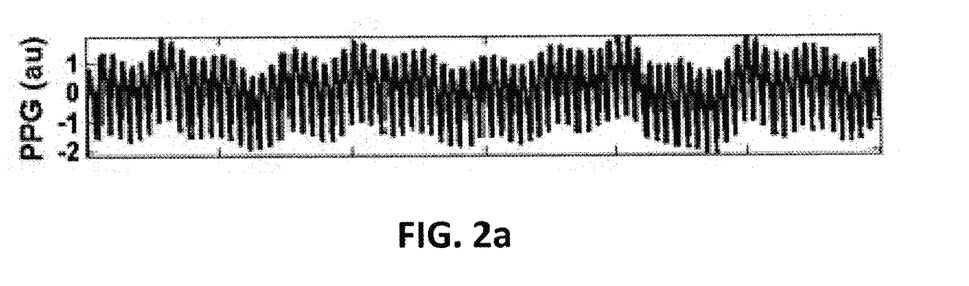
FIGS. 2(a)-(d) show representative PPG signals and extracted values in accordance with an embodiment of the present invention.
Figure 2B:
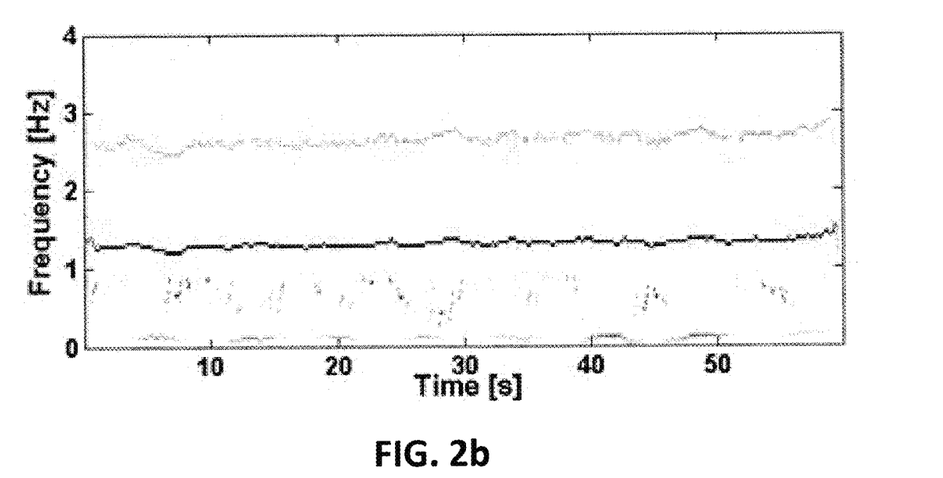
Figure 2C:
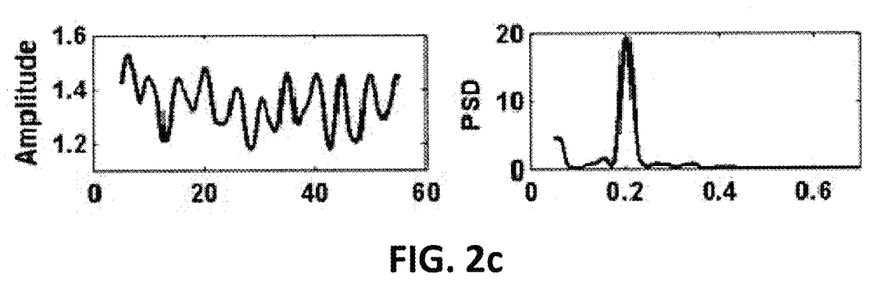
Figure 2D:
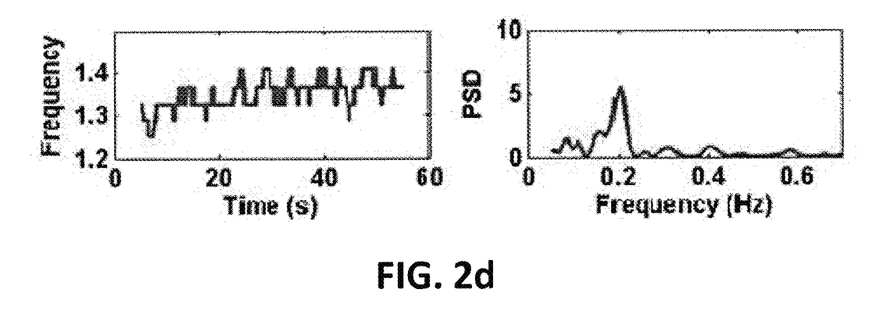

Time-varying and nonlinear dynamics of the respiration variations are accounted for utilizing a high-resolution TFS technique and subsequent extraction of the respiration AM waveforms. As shown in FIG. 2(c), the AM waveforms extracted via the TFS are the dominant periodic component, and are less affected by noise and motion artifacts. Consequently the PSD of the AM waveforms yield the largest spectral peak. That is, FIGS. 2(a)-(d) show representative PPG signals and extracted values. A representative PPG signal recorded at metronome breathing rate of twelve breaths per minute (i.e. 0.2 Hz) is shown in FIG. 2(a) and an estimated TFS using VFCDM with a prominent frequency oscillation seen near heart rate (i.e. 1.3 Hz), e.g. as shown in FIG. 2(b). FIG. 2(c) shows an extracted AM sequence, and FIG. 2(d) shows an extracted FM sequence in the HR band of TFS, shown along with respective corresponding PSDs with a highest obtained peak of 0.2 Hz, i.e. the breathing frequency.

In a preferred embodiment, respiration rate modulates both amplitude and frequency of the PPG signal are recognized, similar to the respiratory sinus arrhythmia modulating the HR signal. See U.S. patent application Ser. No. 11/803,771 to Chon. Using a spectral method with one of the highest resolutions in both the time and frequency domains, allows for extraction of the amplitude (or frequency) modulation (AM) at the heart rate frequency; subsequent PSD of the AM or FM provides the respiratory rate. Thus, the preferred embodiments differ from conventional systems by not performing direct calculations on the PPG signal. Rather, an AM or FM time series is extracted, from which respiratory rates and blood loss are quantified.

Using the AM or FM time series, rather than performing the direct calculation on the PPG signal, reduces the effect of noise/motion artifacts since the extracted AM or FM time series itself become the dominant periodic signal within the narrow heart rate frequency band. The obtained dominant periodic signal reduces the effect of other high and low frequency noise sources, reflects the respiratory variations and provides an amplified spectral peak at the respiratory frequency, as shown in FIG. 2(c).

Accordingly, motion/noise artifacts present in the extracted AM or FM time series do not exist at each time points, resulting in an overall magnitude that is negligible compared to the respiratory peak, as shown in FIG. 2(c).

In a preferred embodiment, respiratory rate was extracted from noninvasive PPG signals based on observations that respiration modulates both amplitude (FIG. 2(a)) and frequency of the PPG signal. Direct estimation of the respiratory rate from the PPG signal using the PSD is not possible, with selection of an appropriate peak being unclear since there are multiple peaks and the spectral magnitude associated with the respiratory rate is among the smallest. Corruption by motion artifacts compounds this problem, creating spectral peaks of equal or larger magnitudes in the vicinity of the peak associated with the respiratory rate. Further, the respiratory rate reflected as either AM or Frequency Modulation (FM) of the PPG signal is highly time varying and difficult to monitor using conventional methods such as the PSD. Thus, the present invention preferably utilizes a high-resolution TFS method, preferably a VFCDM approach.

In a preferred embodiment, the largest amplitude at each time point within the HR band, i.e. approximately 1.3 Hz shown in FIG. 2(b), of the TFS of VFCDM is extracted as an AM sequence, and the corresponding instantaneous frequency for the largest amplitude constitutes the FM sequence. Since they are relatively stationary, as shown in the left panels of FIG. 2(c)-(d), taking the PSD of AM and FM sequences of the HR band allows the respiratory frequency to be determined as the frequency corresponding to the maximum peak in the PSD. This sequence of procedures will be termed as VFCDMppg.

Figure 7:
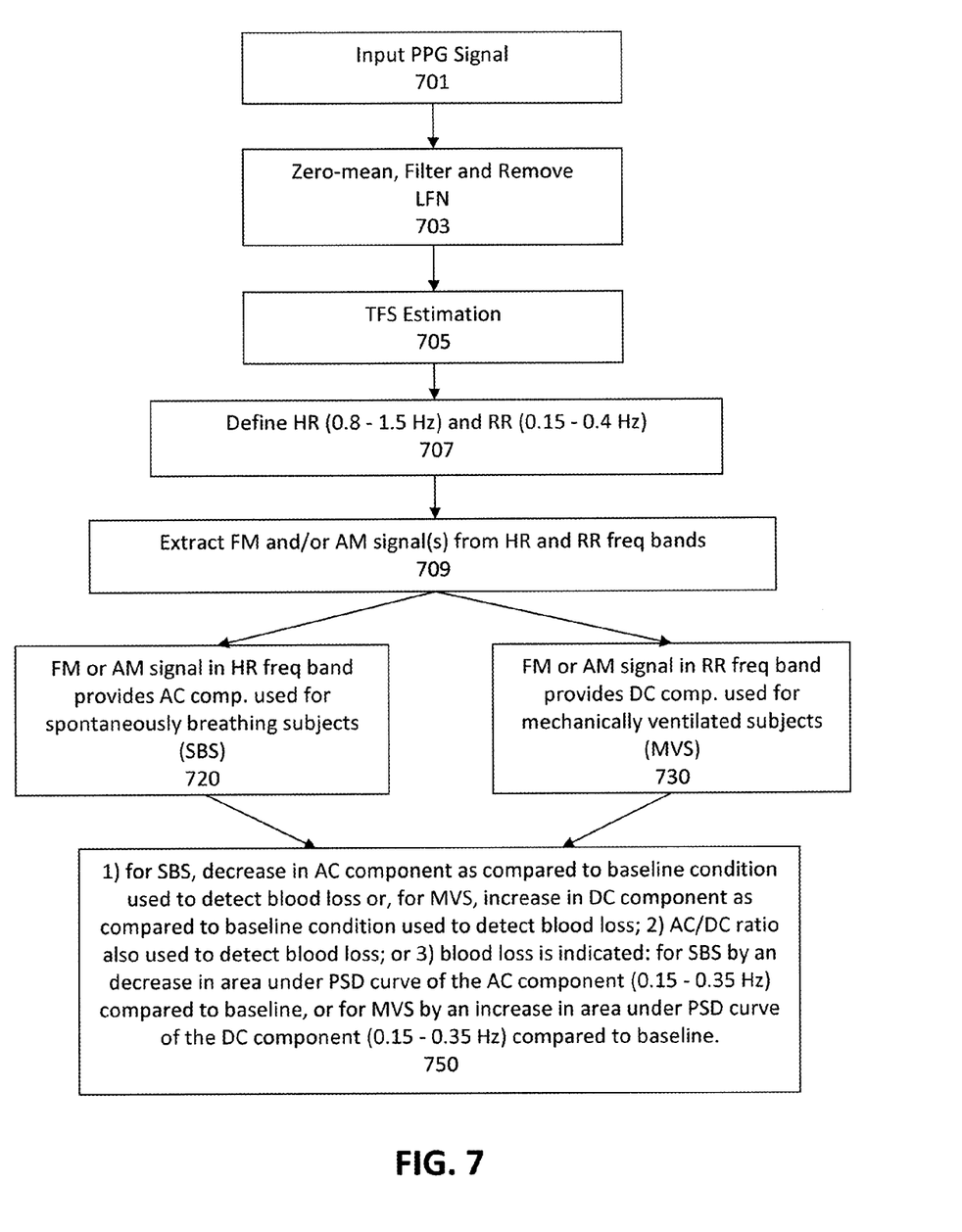
FIG. 7 is a flowchart of a preferred embodiment of the present invention.

As shown in FIG. 7, a PPG signal is input in step 701, and low frequency noise is removed in step 703. In step 705, TFS estimation is performed using VFCDM, and Heart Rate (HR) and Respiratory Rate (RR) frequency bands are defined in step 707. In step 709, FM and AM signals are extracted from the HR and RR frequency bands. For a spontaneously breathing patient, in step 720 the FM or AM signal obtained in the HR frequency band provides an AC component. For a mechanically ventilated patient, in step 730 the FM or AM signal obtained in the RR frequency band provides a DC component.

In step 750, a decrease in the AC component, as compared to a baseline condition, is used to detect blood loss in the spontaneously breathing patient, and an increase in the DC component, as compared to baseline condition, is used to detect blood loss in the mechanically ventilated patient.

A ratio of AC/DC can also be used to detect blood loss. PSD can also be performed of the AC and DC components, with a decrease in an area under an obtained PSD curve of the AC component, in a range of 0.15-0.35 Hz, as compared to the baseline condition indicates blood loss in the spontaneously breathing patient, whereas an increase in the area under the PSD curve of the DC component, in a range of 0.15-0.35 Hz, as compared to the baseline condition indicates blood loss in the mechanically ventilated patient.

In a preferred embodiment, the VFCDMppg is applied for blood loss detection during blood donation in healthy volunteers under metronome, with spontaneous breathing. Results were obtained after two units of blood were withdrawn and re-infused in nine healthy volunteers under metronome and spontaneous breathing, with PPG data recorded from ear, finger and forehead sites. Spectral peak and integrated power about respiratory frequency, i.e. 0.15-0.7 Hz, of the associated PSD of AM and FM sequences of the HR frequency band of the PPG signal underwent statistically significant changes during blood volume loss, with the changes being discernible via the VFCDMppg of the present invention, before statistically significant observable changes in HR and BP. The selected frequency range is appropriate for a normal human breathing rate of 12-20 breaths/min.

Figure 3:
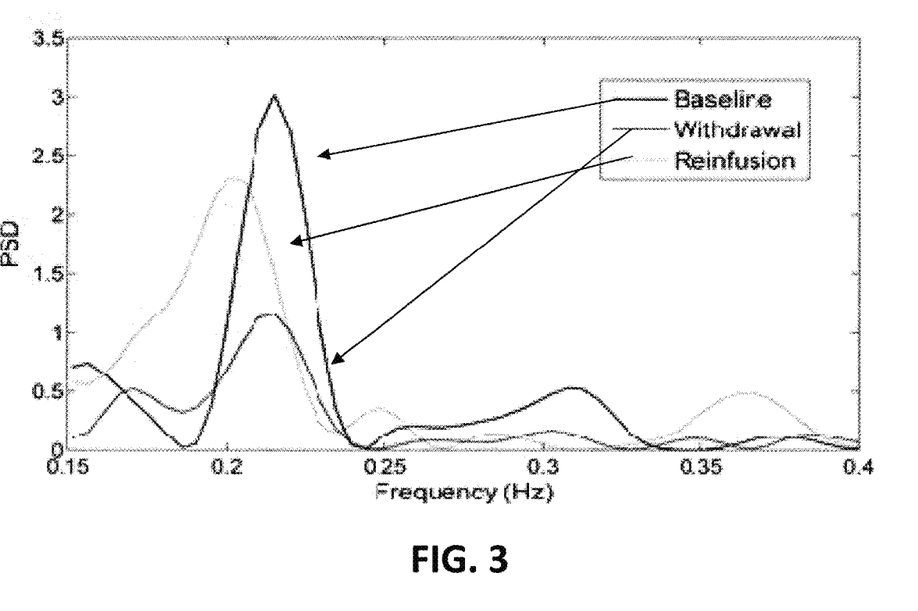
FIG. 3 shows PSDs of modulated sequences derived from cardiac components of ear-PPG signals of a spontaneously breathing representative patient showing baseline, blood withdrawal, and reinfusion periods.

FIG. 3 provides plots of an FM sequence derived PSD's for baseline, withdrawal, and re-infusion, with statistically significant changes in spectral peak and integrated power observed about the respiratory frequency (0.15-0.7 Hz) between baseline and withdrawal conditions. For all nine subjects, a statistically significant decrease ($p<0.05$, $n=9$ subjects) in the respiratory spectral power was observed in both AM and FM series of ear and finger PPG signals after two units of blood withdrawal during metronome-paced breathing. Furthermore, a statistically significant increase was noticed after reinfusion, although the spectral power did not return to the baseline level. Statistically significant changes were similarly observed in the ear-PPG signal during spontaneous breathing with blood withdrawal and reinfusion. Meanwhile, no statistically significant changes occurred in the HR or BP from baseline to withdrawal or from withdrawal to reinfusion. Therefore, the technique of the present invention detects blood loss before the onset of significant changes in HR or BP, by analyzing changes in modulations of only the cardiac frequency, i.e. AC components.

In regard to detection of blood loss during surgical procedure with mechanical ventilation, FIG. 4 shows results of an investigation of continuous changes in instantaneous amplitude modulations present in cardiac as well as respiratory band frequencies of the PPG in patients undergoing surgical procedure with mechanical ventilation. AM sequences of underlying HR and respiration frequency band in the PPG are extracted from the VFCDMppg, referred to herein as the AC and DC components of the PPG, respectively.

Figure 4A:
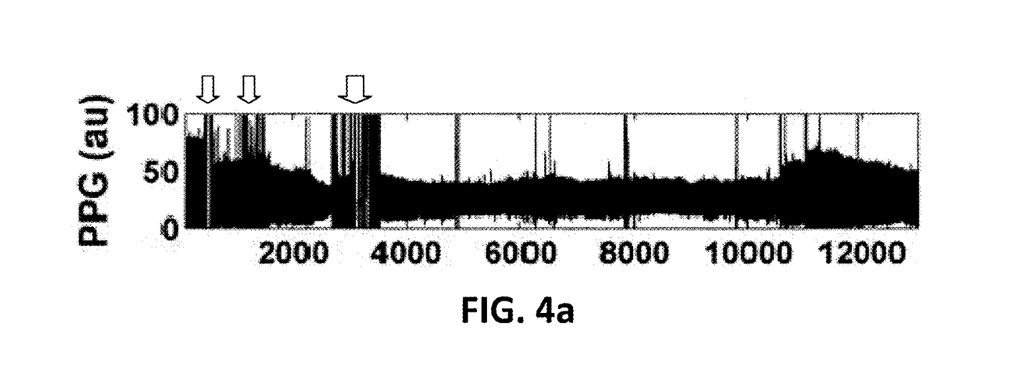
FIGS. 4(a)-(d) show blood loss detection for mechanically ventilated subjects.
Figure 4B:
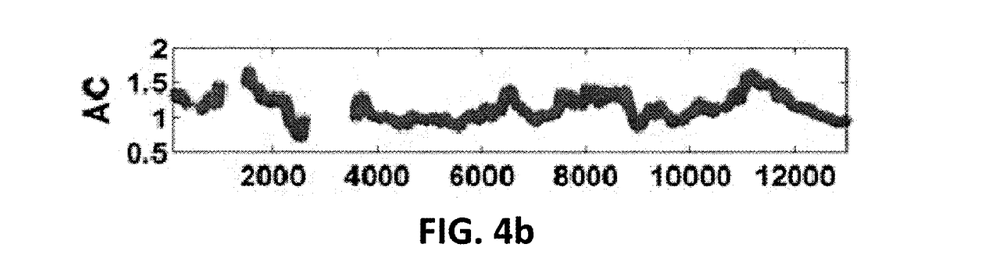
Figure 4C:
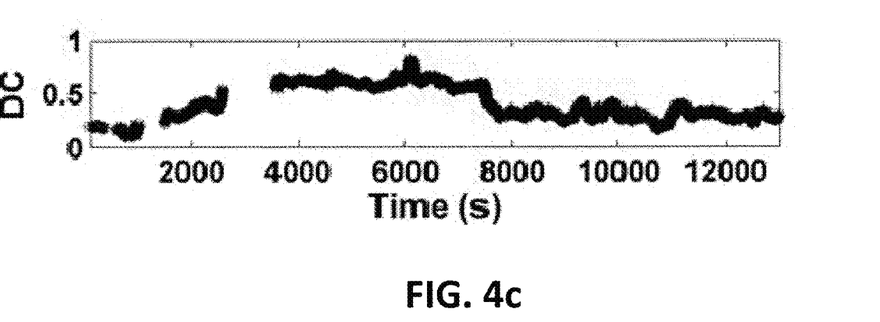

As the AC and DC components of the VFCDMppg are associated with changes in arterial and venous pulsations respectively, the DC/AC ratio includes the effect of both pulsations. Quantification of continuous changes in the DC component of the VFCDMppg provides an indication of changes to intravascular volume. During a surgical procedure in which the patient is mechanically ventilated, the DC component changes provide an improved indication over changes to the AC component. The DC component of the VFCDMppg signal was found to tremendously increase due to the blood volume loss, as shown in FIG. 4($b$), whereas the AC component of the VFCDMppg did not show any substantial changes, as shown in FIG. 4($c$).

In FIG. 4($a$), the PPG is recorded from an ear of an anesthetized patient under mechanical ventilation. The continuous changes of the PPG signal extracted from TFS of VFCDM are shown in FIG. 4($b$) in regard to the AC and in FIG. 4($c$) in regard to the DC components. In FIG. 4($d$) the changes in DC/AC ratio of VFCDMppg, as shown by longer dashes '-' with a scale on the left y axis, are given along with the changes in the Expected Blood Loss (EBL), as shown by smaller dashes ('--') with a scale provided on the right y axis, and fluid in, i.e. an infused fluid level, are shown by short dash-dot-short dash. The baseline value of DC/AC for about three minutes is around fifteen percent. As shown in FIG. 4($d$), the DC/AC ratio increase to 22.42% at a time of 14:53:30, which is a 49.5% increase as compared to baseline, which is a detection of blood loss for mechanically ventilated subjects occurring sixteen and one-half minutes earlier than the actual blood loss detection of 1300 ml by the physicians. Uncontrolled motion artifacts are indicated with arrows in FIGS. 4($a$) and ($d$).

Changes in the DC component indicate dominance of venous modulation caused by mechanical ventilation, attributable to a direct effect of positive pressure ventilation inducing retrograde flow of blood to the PPG. The relative impact of this retrograde flow is greater in the context of hypovolemia; and the venous compliance is increased during hypovolemia, thereby generating a greater change in volume for a given pressure.

In contrast, the changes in the AC component are not augmented by mechanical ventilation. Instead, the AC components are influenced primarily by alterations in venous return to the heart, the impact of which is modulated by compensatory mechanisms; e.g., a decline in venous return due to hypovolemia and/or ventilation is attenuated by prolongation of the cardiac pre-ejection period, increase of cardiac contractility, and alteration of peripheral vascular tone.

Figure 4D:
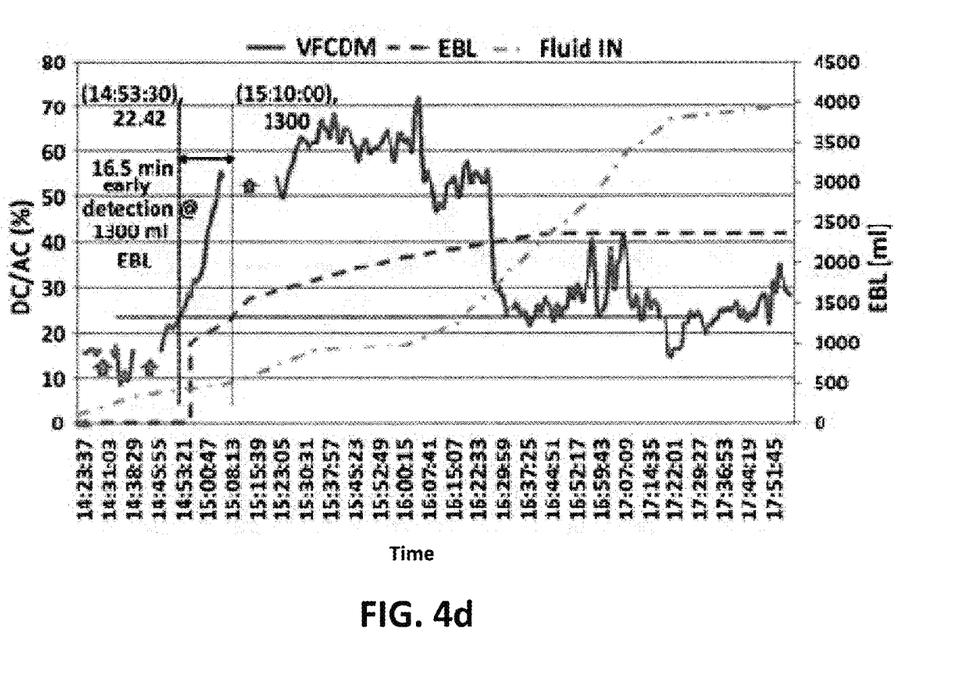

In order to properly account for the strength of the cardiac pulse, the DC/AC ratio is normalized to cardiac pulse strength. In a preferred embodiment, the DC/AC ratio of the VFCDMppg signal is transiently increased more than 3 times above baseline, which reflected the progressive blood volume loss during the surgical procedure, as shown in FIG. 4($d$).

After re-infusion of fluids, the DC/AC ratio showed a recovery towards the baseline. Preliminary results show that detection of blood volume loss for a mechanically ventilated subject occurred 16.5 minutes earlier than the actual blood loss detection of 1300 ml by the physicians, for a chosen blood loss of ~20 cc/kg of body weight as a threshold value to identify a hypovolemic state, as a criterion commonly considered by anesthesiologists to constitute symptomatic blood loss meriting prompt intervention. As indicated by arrows in FIG. 4($a$), a few segments of PPG data are corrupted by extreme motion artifacts, and motion artifact detection/removal was utilized to maintain real-time continuous monitoring.

Figure 5A:
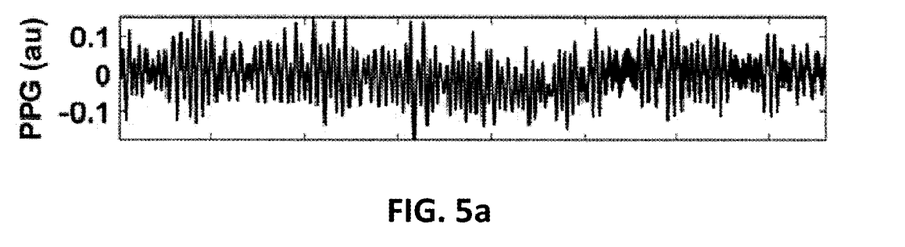
FIGS. 5(a)-(c) show representative ear-PPG data recorded during an Lower Body Negative Pressure (LBNP) experiment.
Figure 5B:
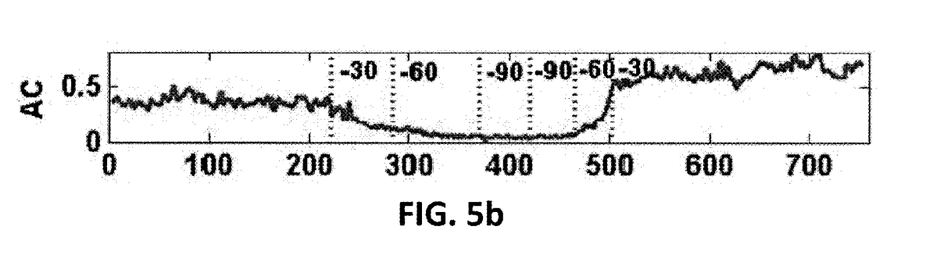
Figure 5C:
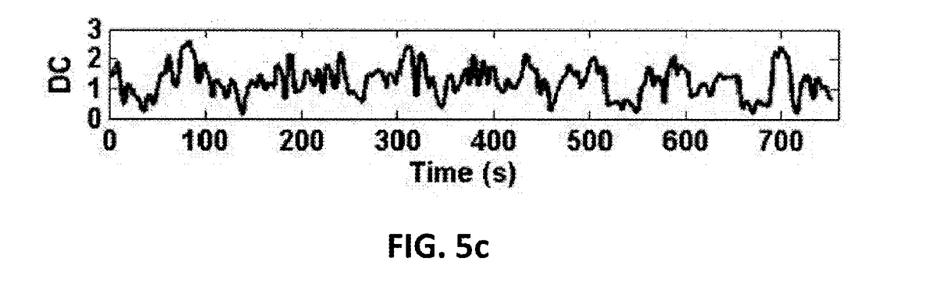

In regard to detection and quantification of simulated hypovolemia, i.e. blood sequestration, during LBNP with spontaneous ventilation, analysis was performed of VFCDMppg modulations during progressive reduction in central blood volume induced by LBNP in healthy subjects with spontaneous ventilation. Three minutes of baseline recording was performed, followed by a gradual decrease of LBNP to −90 mmHg, where the pressure was held for approximately one to two minutes, or until the subject showed presyncopal symptoms. Chamber decompression was then gradually released to baseline. A representative ear-PPG data recorded from one subject during the LBNP experiment is shown in FIGS. 5($a$)-($c$). FIG. 5($a$) shows output of a VFCDM analysis of ear-PPG data recorded during an LBNP experiment, with a gradual decrease in AC components of the PPG signal shown in FIG. 5($b$). The decreasing AC components correspond to an onset and release of chamber decompression (−30 to −90 mmHg), shown by dotted vertical lines in FIG. 5($b$). Changes in AC components of the PPG signal reflect a progressive loss of blood volume simulated by LBNP. Meanwhile, in FIG. 5($c$) no substantial changes in DC components in relation to the LBNP were observed.

The VFCDMppg analysis reveals that the impact of LBNP is reflected in the PPG signal as a decrease in the AC component with no substantial changes in the DC component, as shown in FIGS. 5($b$)-($c$), as observed in conscious subjects, as being consistent with the blood withdrawal study of FIG. 3, where the arterial pulsation is attenuated. Further, a ten-fold decrease in normalized PSD power of the AC components (0.15-0.35 Hz) was observed between LBNP of −90 mmHg and the baseline.

Figure 6:
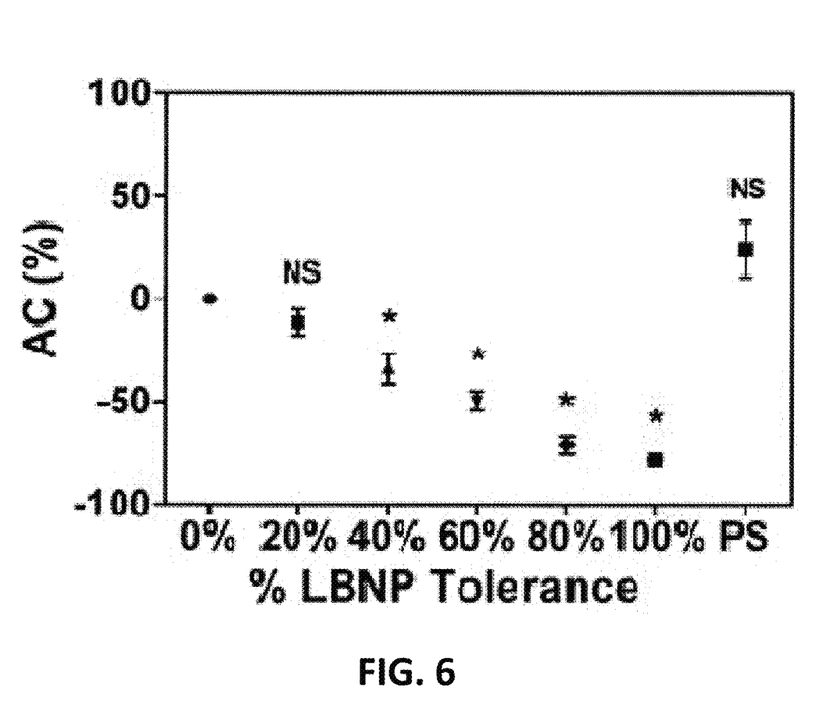
FIG. 6 shows percentage changes in an AC component of VFCDMppg obtained during LBNP experiment.

FIG. 6 shows a linearly graded decrease in AC values with an increased percentage of LBNP tolerance, indicating quantifiable blood loss during spontaneous breathing LBNP experiments. In the LBNP experiment, percentage changes in the AC component of VFCDMppg were obtained from eleven healthy volunteers. Repeated measures an analysis of variants with Tukey's multiple comparison tests was conducted to find the significance levels between baseline (0% LBNP tolerance) and other stages of LBNP experiment, with PS, post symptomatic; NS, not significant; and * $P<0.05$.

In the LBNP experiments, each individual's PPG data was normalized to their maximal capacity of LBNP tolerance by distributing into five stages between a zero percent LBNP tolerance as a baseline and a one-hundred LBNP tolerance as a maximal value, the level at which the subjects showed presyncopal symptoms and the protocol was terminated. The percentage changes in AC and DC components were calculated from VFCDMppg for every stage with respect to the individual's baseline response. Statistical significance with respect to the baseline is observed when % LBNP tolerance was found to be greater than forty percent (>40%). Thus, the changes in AC of VFCDMppg were found very useful for detecting the progressive changes in central blood volume for spontaneously breathing subjects. This result is in contrast to the expansion of compliant veins by mechanical ventilation and hence a sensitive means for assessing augmented change during hypovolemia. A potential for a decline in the magnitude of the response by the highly compliant venous system to the negative aspiratory pressure induced by spontaneous ventilation. In the latter context, hypovolemia may predispose to vein collapse, which would mask further changes. Hence, the degree of change is more difficult to delineate during spontaneous ventilation.

While this invention has been particularly shown and described with reference to preferred embodiments thereof, it will be understood by those skilled in the art that various changes in form and details may be made therein without departing from the scope of the invention encompassed by the appended claims.

What is claimed is:

1. A method for non-invasive monitoring and detection of sudden changes in cardiovascular hemodynamics, the method comprising:
   obtaining a photoplethysmography (PPG) signal from a patient;
   computing, from the PPG signal, a time-frequency spectrum (TFS), the TFS obtained using Complex Demodulation (CDM);
   extracting from the TFS, for a predetermined range of frequencies, time points for the TFS in the predetermined range of frequencies; wherein the predetermined range of frequencies is at least one range of frequencies selected from a range between 0.8 and 1.4 Hz, referred to as a heart rate range and a range between 0.15 and 0.4 Hz, referred to as a respiratory rate band;
   obtaining, from a curve of the time points for the IFS in the predetermined range of frequencies, a curve of instantaneous modulations at the time points in the predetermined range of frequencies, the instantaneous modulations being amplitude modulations; for the range between 0.8 and 1.4 Hz the instantaneous modulations being referred to as AC components; for the range between 0.15 and 0.4 Hz the instantaneous modulations referred to as venous components; and
   detecting impending hypovolemia by one of either by detecting changes in a ratio of the venous components to the AC components, or, for a mechanically ventilated patient, by detecting increases in the venous components.

2. The method of claim 1, wherein, for a mechanically ventilated patient, an indication of hypovolemia is obtained by detecting increases in the venous components of the TFS signal.

3. The method of claim 1,
   wherein an indication of hypovolemia is obtained by detecting changes in a ratio of the venous components to the AC components.

4. The method of claim 3 wherein, for a mechanically ventilated patient, an indication of hypovolemia is obtained by detecting increases in the ratio of the venous components to the AC components.

5. The method of claim 3 wherein, for a spontaneously breathing patient, an indication of hypovolemia is obtained by detecting increases in the ratio of the venous components to the AC components.

6. A system for detecting hypovolemia, the apparatus comprising:
   a computer configured to:
      compute, from a PPG signal, a time-frequency spectrum (TFS), the TFS obtained using Complex Demodulation (CDM);
      extract from the TFS, for a predetermined range of frequencies, time points for the TFS in the predetermined range of frequencies; wherein the predetermined range of frequencies is at least one range of frequencies selected from a range between 0.8 and 1.4 Hz referred to as a heart rate range and a range between 0.15 and 0.4 Hz, referred to as a respiratory rate band;
      obtain, from a curve of the time points for the IFS in the predetermined range of frequencies, a curve of instantaneous modulations at the time points in the predetermined range of frequencies, the instantaneous modulations being amplitude modulations; for the range between 0.8 and 1.4 Hz the instantaneous modulations being referred to as AC components; for the range between 0.15 and 0.4 Hz the instantaneous modulations referred to as venous components; and
      detecting impending hypovolemia by one of either by detecting changes in a ratio of the venous components to the AC components, or, for a mechanically ventilated patient, by detecting increases in the venous components.

7. The system of claim 6 wherein, for a mechanically ventilated patient, an indication of hypovolemia is obtained by detecting increases in the venous components of the TFS signal.

8. The system of claim 6
   wherein an indication of hypovolemia is obtained by detecting changes in a ratio of the venous components to the AC components.

9. The system of claim 8 wherein, for a mechanically ventilated patient, an indication of hypovolemia is obtained by detecting increases in the ratio of the venous components to the AC components.

* * * * *